(12) United States Patent
Allmendinger

(10) Patent No.: US 9,498,168 B2
(45) Date of Patent: Nov. 22, 2016

(54) X-RAY CT SCANNING AND DUAL-SOURCE CT SYSTEM

(71) Applicant: SIEMENS AKTIENGESELLSCHAFT, Munich (DE)

(72) Inventor: Thomas Allmendinger, Forchheim (DE)

(73) Assignee: SIEMENS AKTIENGESELLSCHAFT, Munich (DE)

(*) Notice: Subject to any disclaimer, the term of this patent is extended or adjusted under 35 U.S.C. 154(b) by 243 days.

(21) Appl. No.: 14/183,579

(22) Filed: Feb. 19, 2014

(65) Prior Publication Data

US 2014/0247917 A1    Sep. 4, 2014

(30) Foreign Application Priority Data

Mar. 1, 2013  (DE) .................. 10 2013 203 541

(51) Int. Cl.
*A61B 6/03* (2006.01)
*A61B 6/00* (2006.01)

(52) U.S. Cl.
CPC ............... *A61B 6/035* (2013.01); *A61B 6/032* (2013.01); *A61B 6/4014* (2013.01); *A61B 6/482* (2013.01)

(58) Field of Classification Search
USPC ............ 378/9, 15, 134, 137, 19, 4, 901
See application file for complete search history.

(56) References Cited

U.S. PATENT DOCUMENTS

| | | | |
|---|---|---|---|
| 6,118,839 A | 9/2000 | Dafni et al. | |
| 6,580,777 B1 | 6/2003 | Ueki et al. | |
| 7,187,748 B2 | 3/2007 | Hoffman | |
| 7,203,268 B2 | 4/2007 | Yahata | |
| 7,627,081 B2 | 12/2009 | Bontus | |
| 7,945,012 B2 | 5/2011 | Ye et al. | |
| 2003/0108146 A1* | 6/2003 | Malamud | A61B 6/032 378/19 |
| 2004/0081270 A1* | 4/2004 | Heuscher | A61B 6/032 378/4 |
| 2007/0290138 A1* | 12/2007 | Scholz | A61B 6/032 250/363.02 |
| 2010/0091940 A1* | 4/2010 | Ludwig | A61B 6/025 378/22 |

FOREIGN PATENT DOCUMENTS

| | | |
|---|---|---|
| DE | 102006027221 A | 12/2007 |
| JP | 2007007217 A | 1/2007 |

OTHER PUBLICATIONS

Morneburg H.; "Bildgebende Systeme für die medizinische Diagnostik"; Publicis MCD Verlag; 3. wesentlich Überarbeitete und erweiterte Auflage; pp. 254-261; ISBN: 3-89578-002-2; 1995. English Abstract.

(Continued)

*Primary Examiner* — Phillip A Johnston
*Assistant Examiner* — Hsien Tsai
(74) *Attorney, Agent, or Firm* — Harness, Dickey & Pierce, P.L.C.

(57) ABSTRACT

A method is disclosed for x-ray CT scanning with a dual-source system, in which two radiation bundles are each delimited by diaphragms such that these radiation bundles are free of mutual points of intersection at least in the examination object. An embodiment of the invention also relates to a dual source CT system, including a controller configured to control radiation-delimiting diaphragms, which delimit and align the radiation bundles such that these run free of mutual points of intersection at least in the examination object.

25 Claims, 9 Drawing Sheets

(56) References Cited

OTHER PUBLICATIONS

German Office Action for German Applicaiton 10 2013 203 541.1 Dated Nov. 11, 2013.

German Priority Document German Application 10 2013 203 541.1 Filed Mar. 1, 2013.

* cited by examiner

X-RAY CT SCANNING AND DUAL-SOURCE CT SYSTEM

PRIORITY STATEMENT

The present application hereby claims priority under 35 U.S.C. §119 to German patent application number DE 102013203541.1 filed Mar. 1, 2013, the entire contents of which are hereby incorporated herein by reference.

FIELD

At least one embodiment of the invention generally relates to x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated.

Furthermore, at least one embodiment of the invention also generally relates to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by diaphragms is aligned toward the respectively assigned multi-row detector.

BACKGROUND

A method and a dual-source CT system used for this purpose are generally known. With such scanning methods and such CT systems having two tubes in a 90° arrangement, operation in the dual tube mode inevitably results in the development of transverse scatter on the object, which, for geometric reasons, can also not be screened out by a scattered radiation grid operating in a two-dimensional manner across the detectors and is therefore measured on the detector as an additional signal. If the amounts of this transverse scatter are not corrected, this inevitably results in artifacts in the image, which, particularly during a two spectra dual-source scan, in other words during dual-energy operation, have a sustained adverse effect on the evaluation and deliver artifact-loaded results.

For this reason, algorithms have been developed, which attempt to estimate and correct these scattered radiation amounts. Technical hardware solutions also exist for measuring and correcting the scattered radiation amounts, such as for instance scatter monitors, reduced collimation for measuring the scattered radiation amounts in the edge lines. In particular, the recording modes based on edge line correction were used in previously existing devices to deliver high-quality results.

For a device with a scattered radiation grid operating in a two-dimensional manner, this type of data acquisition and correction is however not possible.

SUMMARY

At least one embodiment of the invention is directed to a method and/or an x-ray CT scanning with two emitter-detector systems and a dual-source CT system which, during the scanning process, have a reduced tendency toward the formation of artifacts in the CT displays produced therefrom.

Advantageous developments of the invention are the subject matter of subordinate claims.

The inventor has identified that a special form of data acquisition and control of the scanning radiation bundle may allow for extensive suppression of the scattered radiation amounts. The key to this is an asymmetric operation of the two detectors with respect to the superimposed rows, which, in combination with the two-dimensional scattered radiation grid, result in a strong suppression of the scattered radiation amounts in the respective other detector. This is effected by guidance of the scanning beams such that the radiation bundle of both emitter-detector systems no longer has points of intersection.

To this end, a CT system is developed in at least one embodiment, in which the detector systems and/or the focal points of the emitter are offset relative to one another in the z-direction to such a degree that, despite using a shared gantry, overlaps are prevented between the two radiation bundles of the emitter-detector systems. As a result, the appearance of scattered radiation in the radiation path of the one emitter-detector system is prevented by radiation from the respective other emitter-detector system. The other scattered radiation essentially always produced in both systems can then be suppressed by scattered radiation grids operating in a two-dimensional manner, when considered purely geometrically and in a first approximation. The advantage of such an embodiment of a CT system lies in the used multi-row detectors being able to be used over their entire surface. Nevertheless, this advantage is thus gained in that a simultaneous scanning of a region is no longer possible by two radiation bundles only disposed at different angles.

The inventor proposes improving an x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated. In accordance with at least one embodiment of the invention, the two radiation bundles are to be delimited by the diaphragms respectively such that these radiation bundles are free of mutual points of intersection, at least in the examination object.

Finally, a method is disclosed. In at least one embodiment includes a method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner, the method comprising: generating, during the scanning process between each of the respective focal points and an opposing one of the two detectors of each of the two emitter-detector systems, a radiation bundle diverging in two dimensions and delimited by emitter-side diaphragms, wherein the two radiation bundles are delimited by the diaphragms, respectively, such that the radiation bundles are free of mutual points of intersection at least in the examination object.

BRIEF DESCRIPTION OF THE DRAWINGS

The invention is described in more detail below on the basis of preferred example embodiments with the aid of the figures, wherein only the features required to understand the invention are shown. The following reference signs are used: 1: CT system; 2: x-ray tube; 2.1: controllable diaphragm; 2.2: focal point; 3: multi-row detector; 4: x-ray tube; 4.1: controllable diaphragm; 4.2: focal point; 5: multi-row detector; 6: gantry housing; 7: examination object; 8 patient couch; 9: system axis; A, B: emitter-detector system; D: detector; G: scattered radiation grid; K tilting apparatus; M: center line of the detectors; Prg1-Prgn: computer programs; R: x-ray tube; RA: anode; RB: diaphragm; RF: focus; S,SA,SB: radiation bundle/beam cone; UM, U', U'': peripheral lines; V: displacement apparatus; κ: tilting angle.

In detail.

DETAILED DESCRIPTION OF THE EXAMPLE EMBODIMENTS

Figure 1:
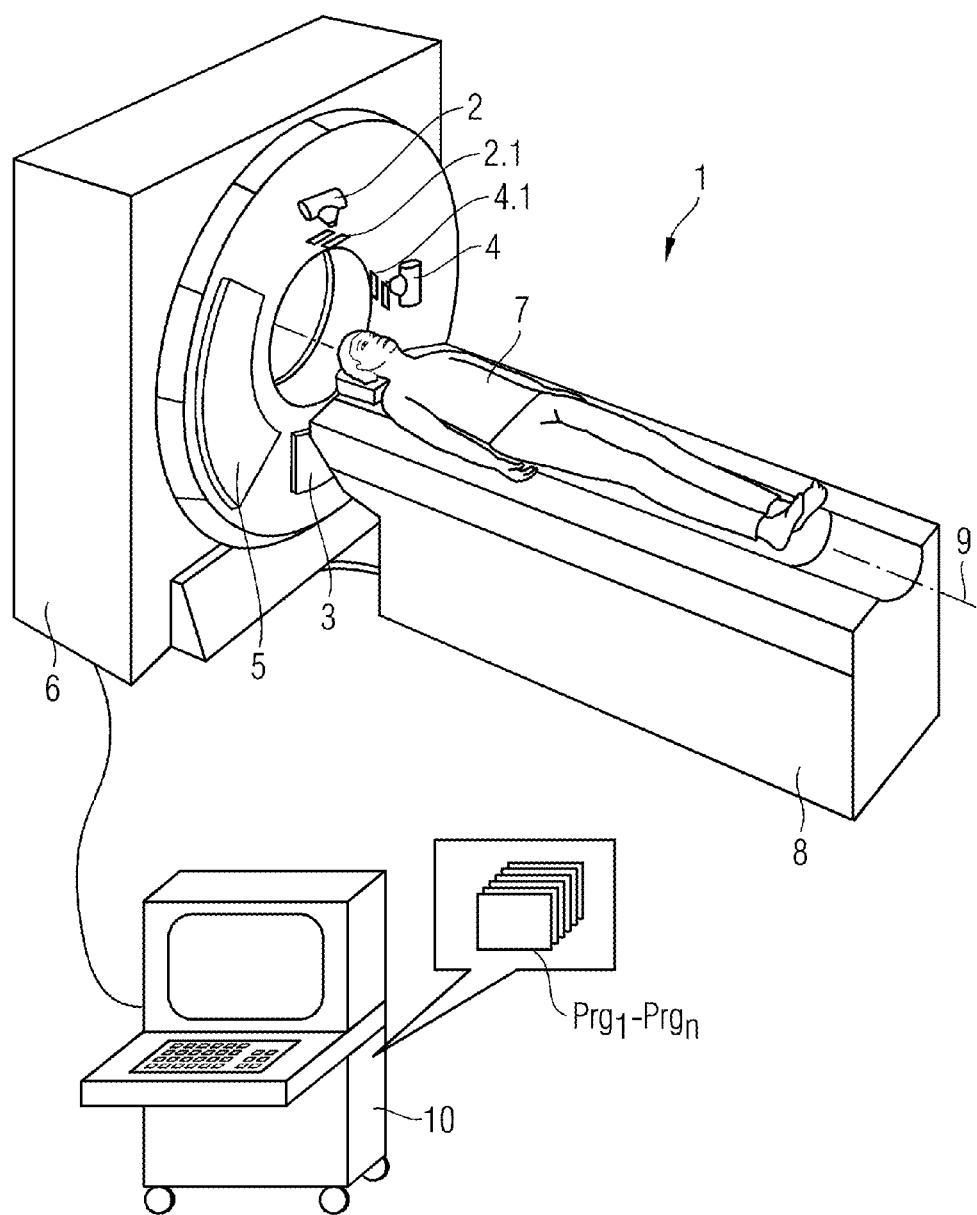
FIG. 1 shows a dual-source CT system

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The inventor has identified that a special form of data acquisition and control of the scanning radiation bundle may allow for extensive suppression of the scattered radiation amounts. The key to this is an asymmetric operation of the two detectors with respect to the superimposed rows, which, in combination with the two-dimensional scattered radiation grid, result in a strong suppression of the scattered radiation amounts in the respective other detector. This is effected by guidance of the scanning beams such that the radiation bundle of both emitter-detector systems no longer has points of intersection.

To this end, a CT system is developed in at least one embodiment, in which the detector systems and/or the focal points of the emitter are offset relative to one another in the z-direction to such a degree that, despite using a shared gantry, overlaps are prevented between the two radiation bundles of the emitter-detector systems. As a result, the appearance of scattered radiation in the radiation path of the one emitter-detector system is prevented by radiation from the respective other emitter-detector system. The other scattered radiation essentially always produced in both systems can then be suppressed by scattered radiation grids operating in a two-dimensional manner, when considered purely geometrically and in a first approximation. The advantage of such an embodiment of a CT system lies in the used multi-row detectors being able to be used over their entire surface. Nevertheless, this advantage is thus gained in that a simultaneous scanning of a region is no longer possible by two radiation bundles only disposed at different angles.

The inventor also proposes at least one embodiment directed to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by the diaphragms is aligned toward the respectively assigned multi-row detector. The diaphragms are then controlled in at least one embodiment, to delimit and align the two radiation bundles such that these radiation bundles run free from mutual points of intersection, at least in the examination object.

In another inventive variant of at least one embodiment, the currently usual structure of a dual-source CT system having two multi-row detectors arranged on a shared gantry and in each instance focal points centrally facing the multi-row detectors is assumed. A one-sided clipping of the radiation bundle emitted by the focal points to the respective detector with the aid of diaphragms attached in the region of the x-ray tube to approximately half of the opening angle of the radiation bundle in the z-direction can be achieved in that the two radiation bundles no longer intersect. Accordingly, each detector is also only still irradiated partially, when viewed in the z-direction, so that the detector in the peripheral direction continues to be fully used, but only a narrower part in the z-direction is used and read out in the z-direction.

In an advanced variant of at least one embodiment, the focal point of the radiation bundles can be removed in the z-direction from one another for improved separation of the radiation bundle. This results in the usable surface of the detector being widened further. Alternatively, the detectors can also be displaced towards one another in the z-direction or both measures can be combined with one another.

Since, due to the relative displacement of focal point and detector in the z-direction, the incident direction of the individual beams per detector element are changed and possibly are no longer adjusted to the existing scattered radiation grid, the detector can also be tilted simultaneously with the change in the radiation direction of the radiation bundle, so that despite a change in the radiation direction, an optimum alignment is always retained between the detector and the focal point.

Accordingly, the inventor proposes improving an x-ray CT scanning of an examination object with two emitter-detector systems arranged at different angles on a shared gantry of a CT system, wherein each emitter has a focal point and each detector is embodied as a multi-row detector having a scattered radiation grid operating in a two-dimensional manner, and during the scanning process between each focal point and the opposing detector of each emitter-detector system, a radiation bundle diverging in two dimensions and delimited by emitter-side diaphragms is generated. In accordance with at least one embodiment of the invention, the two radiation bundles are to be delimited by the diaphragms respectively such that these radiation bundles are free of mutual points of intersection, at least in the examination object.

In a first embodiment variant, the two focal points, such as is currently usual with a dual-source CT, can run on a shared peripheral line. In current CT systems, this peripheral line lies centrally with respect to the opposing detector. Therefore in the prior art, the opening angle of the beam cone is arranged in the z-direction such that it extends symmetrically with respect to a vertical central radiation between the center point of the detector surface and the opposing focus. With the inventive embodiment of a dual-source CT with two detectors arranged symmetrically in the z-direction having central peripheral lines, which run on a shared circular surface around the system axis, the two radiation bundles are superimposed opposite one another in the z-direction such that the one radiation bundle of the one emitter-detector system is reduced in size from one side toward the center, whereas the other radiation bundle of the other emitter-detector system is reduced in size from the other side toward the center. Accordingly, the usable or used surface reduces on the multi-row detector. Such a procedure is generally possible with currently existing dual-source CT systems, without having to perform special reconstructions, since such systems in most instances already have a variable diaphragm system for the beam cone.

A central point is here the asymmetric superimposition of the two detectors of a dual tube system with 2D scattered radiation grid for the spatial separation of the rows superimposed in the respective other detector and the reduction in transverse scatter amounts which results therefrom. It is also possible in this way to obtain dual-energy recordings with a high quality in a 2D scattered radiation grid geometry.

Another variant of at least one embodiment of the inventive method resides in the focal points of the two emitter-detector systems being guided onto two separate peripheral lines, wherein the two separate peripheral lines of the focal points then preferably form circular surfaces, which, when viewed in the z-direction, each run offset with respect to the center line of the detectors. This embodiment improves the intersection-free separation of the two beam cones of the two emitter-detector systems. The detector surface, in the case of multi-row detectors arranged on the same peripheral line, can basically be enlarged or an even better separation of the two radiation bundles can be achieved.

The inventor proposes accordingly, in the case of focal points which are not arranged offset in the z-direction, also in one variant of at least one embodiment of the method that the two radiation bundles are delimited in the z-direction such that they only irradiate part of their multi-row detector, preferably only half or a smaller surface. Accordingly, only the irradiated part of the detectors can be used in each instance for determining the radiation attenuation.

It is also advantageous if the focal points are set with respect to their z-coordinates within the respectively irradiated part of the detectors of the associated emitter-detector system.

Furthermore, the two radiation bundles are to radiate their detectors entirely in respect of the peripheral direction. In other words, the additional superimposition of the radiation bundle only takes place in the z-direction, so that the entire opening angle of the radiation bundle is also retained in the peripheral direction, in other words, the row length of the detectors is used entirely.

In a further embodiment variant of the x-ray CT scanning, the inventor proposes aligning at least one of the detectors by tilting the same with respect to the z-axis toward its focus which is offset in the z-direction. Since the detectors have two-dimensional scattered radiation grids, which limit or include the individual beams between the focus and detector element very precisely, a displacement of the focal point in the z-direction can generate a partial shading of the beams on account of the alignment of the scattered radiation grid which is no longer correct. Such a shading can however be prevented if, at the same time as offsetting the focal point in the z-direction, a tilting of the detector element also takes place, which aligns the detector further toward the focal point. If in the process, a mutual offset of the detectors is effected in the z-direction, the radiation bundle separates again even better and less scattered radiation from the respective other emitter-detector system is measured.

The inventor also proposes at least one embodiment directed to a dual-source CT system for scanning an examination object, comprising two emitter-detector systems arranged at different angles on a gantry with, in each instance, at least one x-ray tube, which forms a focal point during operation, which rotates on a peripheral line about a system axis running in the z-direction, and a multi-row detector likewise rotating about the system axis, the detector rows of which run in the peripheral direction, having a scattered radiation grid operating in a two-dimensional manner, wherein, based on the respective focal point, a radiation bundle delimited by the diaphragms is aligned toward the respectively assigned multi-row detector. The diaphragms are then controlled in at least one embodiment, by a device and/or module, such as a controller (which can include a microprocessor for example) and/or control module for example, configured to delimit and align the two radiation bundles such that these radiation bundles run free from mutual points of intersection, at least in the examination object.

In this case provision is made in at least one embodiment of one variant for a focal point which can be positioned differently in the z-direction to be present for at least one multi-row detector. This can be effected for instance in that at least two emitters with a focal point positioned differently in the z-direction are arranged on the gantry for at least one multi-row detector. Alternatively, an emitter with a focal point which can be displaced in the z-direction can also be provided for at least one multi-row detector. Here the focal point can be displaced for instance by displacing the entire x-ray tube itself with the aid of a corresponding apparatus.

Alternatively, the emitter may comprise a rotatable cylindrical anode with an axis of rotation, so that for displacement of the focal point, only the electrons generating the focal point have to strike another point on the cylinder surface of the anode. Only the electron radiation which generates the focal point is therefore displaced in the process. As a result, shifts in weight advantageously do not occur, which would otherwise have to be balanced out in order to prevent imbalances on the gantry.

Furthermore, in a special embodiment, the axis of rotation of the cylindrical anode can be arranged tilted at the same angle relative to the system axis as the associated multi-row detector is tilted, wherein a tilting apparatus is also provided for at least one multi-row detector, said tilting apparatus tilting the multi-row detector relative to the system axis and the gantry. It is herewith possible, when tilting the multi-row detector and simultaneously displacing the focal point, to keep the stereometric relationships between the detector and focal point the same, so that an existing scatter radiation grid furthermore remains optimally aligned toward the focal point.

A displacement apparatus can likewise also be provided for at least one emitter-detector system, said displacement apparatus displacing at least one multi-row detector in the z-direction. Such a displacement apparatus can also be combined with the tilting apparatus.

Alternatively, a displacement apparatus can be provided for at least one emitter-detector system, said displacement apparatus displacing at least one multi-row detector with its focal point in the z-direction. A translation of the detector in the z-direction thus takes place with a simultaneous translation of the focal point, not necessarily the x-ray tube.

Finally, the dual-source CT system can also be embodied such that a displacement apparatus is provided for at least one emitter-detector system, said displacement apparatus displacing at least one emitter-detector system in the z-direction.

An embodiment of an inventive dual-source CT system 1 is shown in FIG. 1 in a schematic 3D representation. The system 1 essentially includes a gantry housing 6, in which a gantry (not shown explicitly) is disposed, to which are fastened two emitter-detector systems 2, 3 and 4, 5 arranged at different angles about 90° are fastened. Each emitter-detector system includes an x-ray tube 2 or 4 and a multi-row detector 3 or 5 arranged opposite thereto. Controllable diaphragms 2.1 or 4.1 are arranged between the focal points generated in the x-ray tubes 2 or 4 and the measuring field or the examination object 7, here a patient, with which the beam cone originating from the respective focal point can be limited at least in the direction of the system axis 9 (=z direction) for an inventive mode of operation. Aside from the controller of the CT and the data acquisition, the special controller (including a microprocessor, for example) of the diaphragms 2.1, 4.1 and the inventive data acquisition is executed by the control system 10, wherein programs Prg1-Prgn are stored herefor which are executed during operation. In the variant of the inventive CT system 1 shown here, these bring about a mutual superimposition of the two beam cones exclusively in the z-direction, so that the beam cones no longer intersect and only part of the detectors, which is also actually irradiated, is read out. Since no points of intersection are still present between the two beam cones, there are also no more nodes on which scattered radiation from an emitter-detector system could be generated, which runs along the radiation paths in the other emitter-detector system. Accordingly, the scattered radiation portion reduces drastically and artifacts produced by scattered radiation are prevented accordingly.

It is essentially particularly advantageous to embody an embodiment of the inventive method within the scope of a spiral scan, in which the examination object, here a patient 7, is continuously moved through the measuring field during the rotational scanning by the emitter-detector systems with the aid of the patient couch 8. Nevertheless, the invention can also be used in conjunction with a successive circular scanning.

Figure 2:
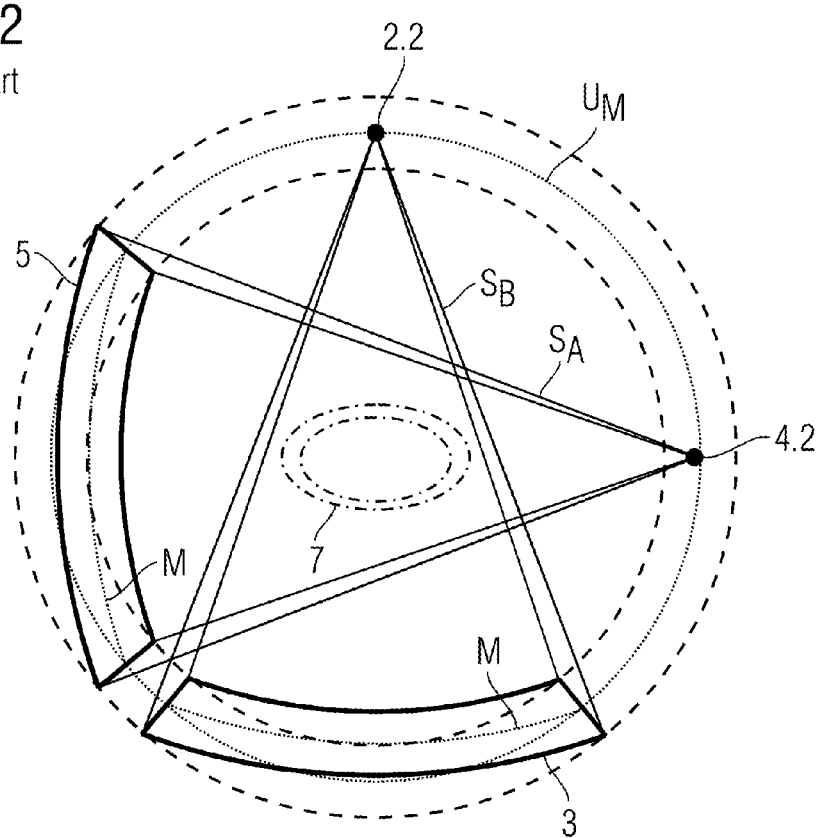
FIG. 2 shows a schematic 3D view of a dual-source CT system according to the prior art from the front.
Figure 3:
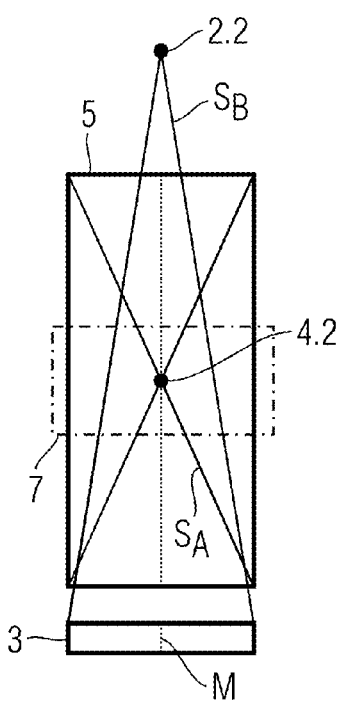
FIG. 3 shows a schematic side view of the CT system from FIG. 2.

In order to explain an embodiment of the invention, a CT system adjusted in accordance with the prior art having emitter-detector systems A and B arranged at different angles on a gantry, is shown in FIGS. 2 and 3, including a multi-row detector 3 and focal point 2.2 or multi-row detector 5 and focal point 4.2 assigned to one another respectively. FIG. 2 shows the emitter-detector systems in a view from the system axis direction and FIG. 3 shows the same in a lateral view at right angles to the system axis. As is apparent, the two beam cones SA and SB intersect, the indices correspond to the emitter-detector systems A and B, in the region of the examination object 7, such that despite an existing, not explicitly indicated—two-dimensional scattered radiation grid, scattered radiation is entered into the respective other emitter-detector system. Both focal points 2.2 and 4.2 move here on a central peripheral line UM. On the circle formed by the peripheral line UM, the center lines M of the detectors 3 and 4 are also disposed.

Figure 4:
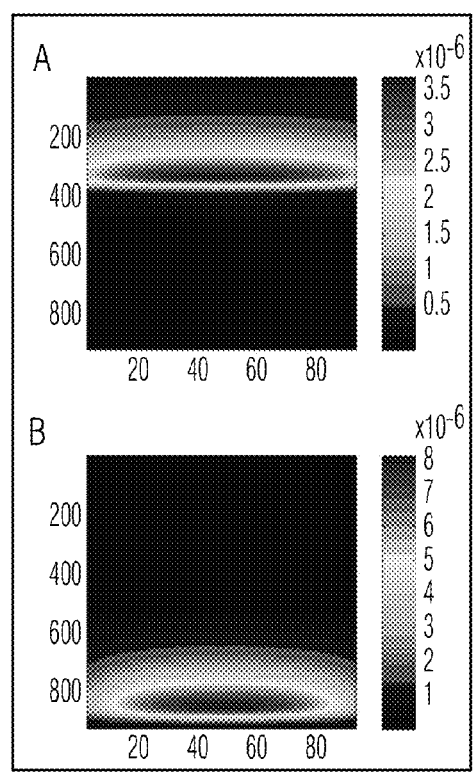
FIG. 4 shows a scattered radiation entry into the emitter-detector systems A+B from the respective other system B+A in a first angle of rotation of the gantry according to FIG. 2.
Figure 5:
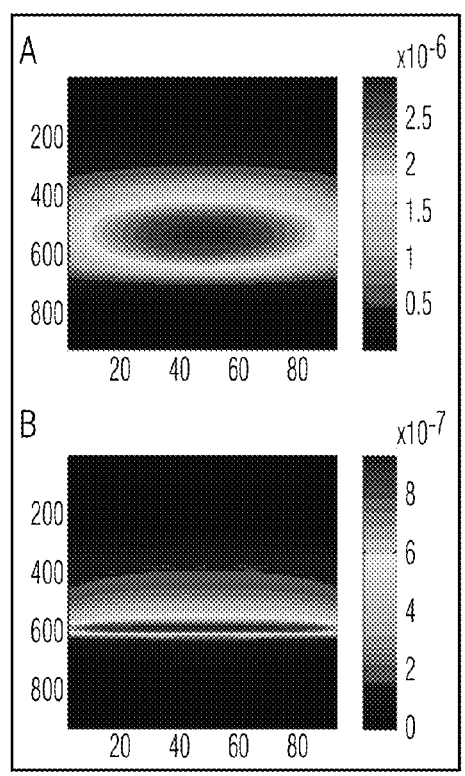
FIG. 5 shows a scattered radiation entry into the emitter-detector systems A+B from the respective other system B+A in a second angle of rotation of the gantry.

The quantity of scattered radiation entered respectively from the other emitter-detector system is clarified in FIGS. 4 and 5, which—recorded at different angles of rotation of the gantry with a non-rotationally symmetrical phantom, indicate the entered scattered radiation intensity on the detectors with 96 lines and 920 rows. The original colored scale of the radiation intensity is indicated in each instance as bars to the right adjacent to the detector. The association with the respective emitter-detector system A or B is likewise indicated adjacent to the detector.

Figure 6:
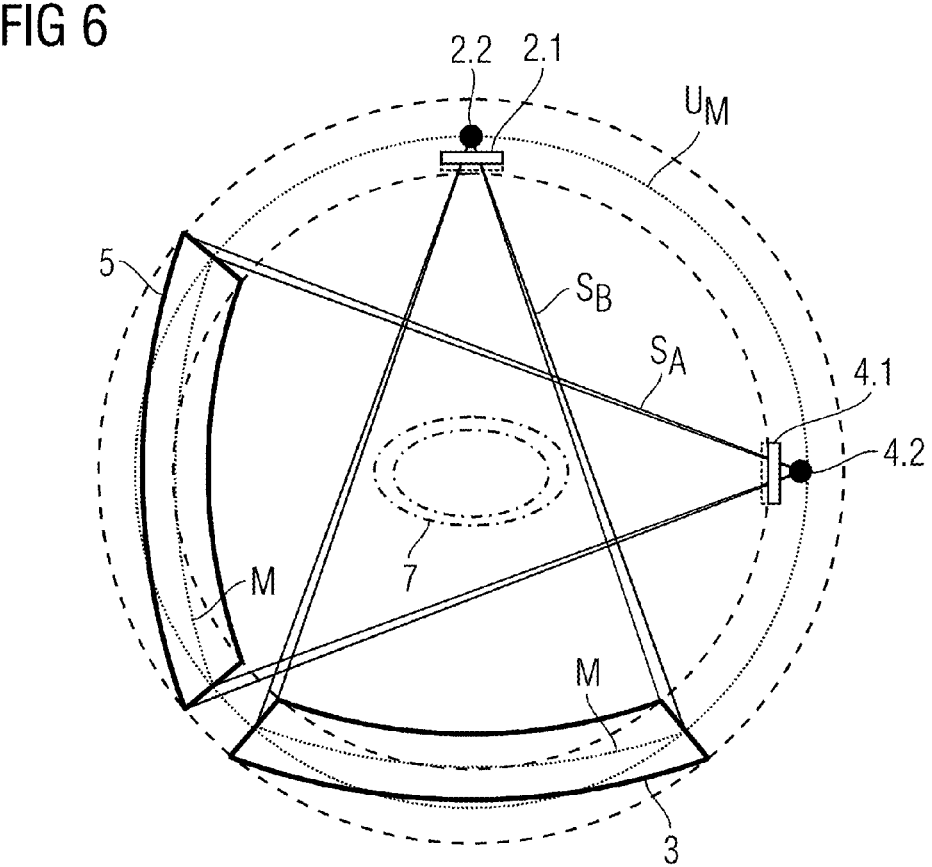
FIG. 6 shows a schematic 3D view of a dual-source CT system with focal points running on a peripheral circle and mutually restricted beam cones.
Figure 7:
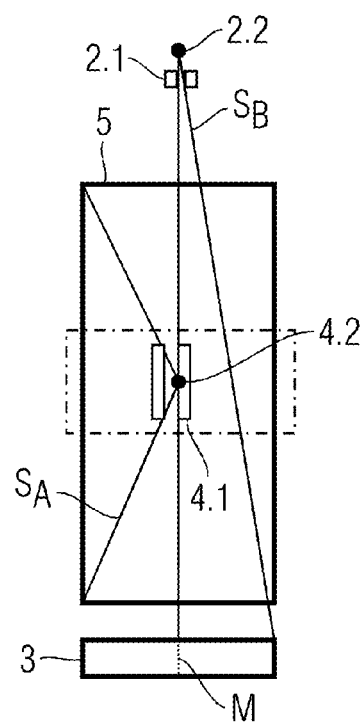
FIG. 7 shows a schematic side view of the CT system from FIG. 6.

In accordance with an embodiment of the invention, the interfering scattered radiation entry can be reduced, by the beam cone being manipulated and arranged such that points of intersection are prevented between the beam cones. To this end, a simple example is show in FIGS. 6 and 7. The representation of the emitter-detector system A and B corresponds to FIGS. 2 and 3, but the two beam cones SA and SB are halved by a corresponding, mutual superimposition in each instance in the z-direction along the peripheral direction, so that each beam cone SA and SB only still irradiates half of its detector 5 or 3. As apparent from FIGS. 6 and 7, the radiation bundles therefore no longer intersect.

Figure 8:
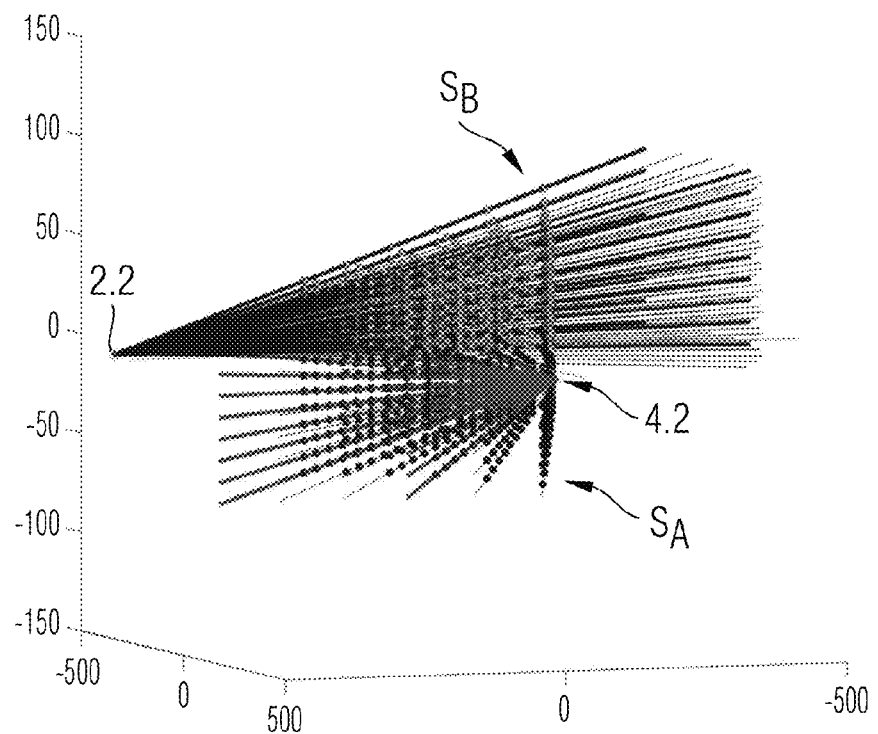
FIG. 8 shows a 3D representation of the radiation bundle from FIG. 6.

Another three-dimensional representation of the two superimposed radiation bundles SA and SB is shown in FIG. 8.

Figure 9:
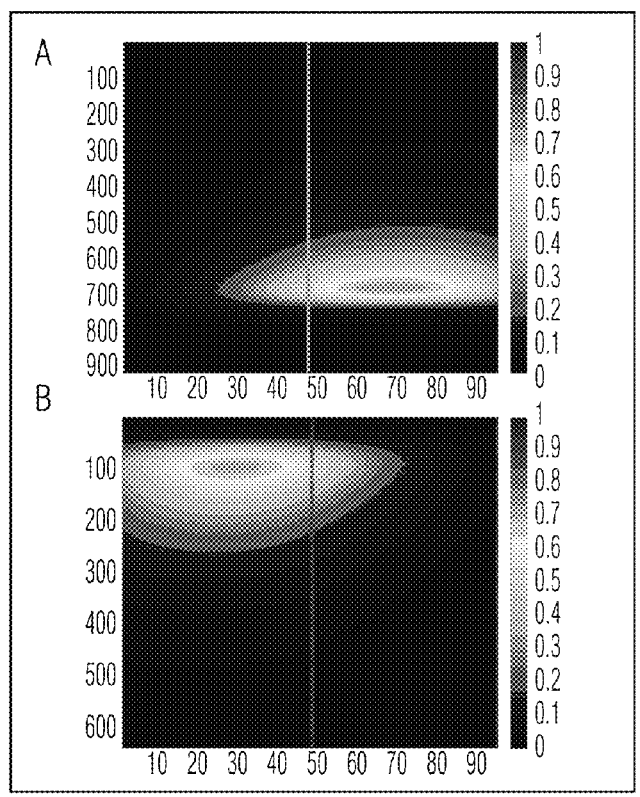
FIG. 9 shows a scattered radiation entry into the emitter-detector systems A+B from the respective other system B+A with a beam cone arrangement according to FIG. 6.

The scattered radiation entry into the respective other detector reduced hereby is shown in FIG. 9, which clarifies the scattered radiation entry according to FIGS. 4 and 5.

Figure 10:
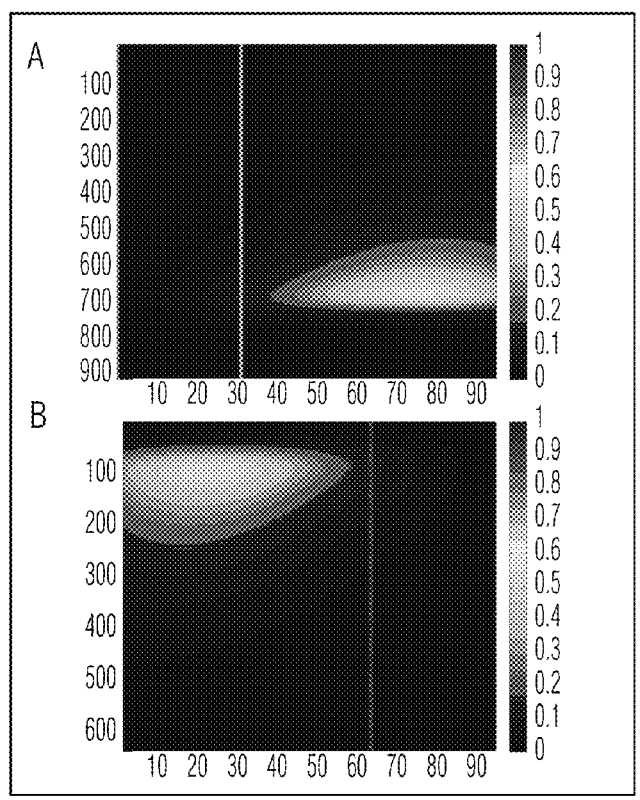
FIG. 10 shows a scattered radiation entry into the emitter-detector systems A+B from the respective other system B+A with a beam cone arrangement according to FIG. 6, nevertheless with a further restriction of the beam cone to a third of the detector surface.

While a superimposition of the beam cone is assumed in FIG. 9 up to the center of the respective detector, FIG. 10 shows the result of a continuous superimposition, so that each detector is only irradiated and used to approximately a third of its width. Accordingly, an improved separation of the radiation bundle is achieved and the proportion of the scattered radiation reverts back to approximately zero in the part of the detector still used respectively for scanning purposes.

Further inventive variants of the embodiment of a dual-source CT system are shown in FIGS. 11 to 14, the aim of which is in each instance to bring about as good a mutual separation of the radiation bundle as possible from the two emitter-detector systems disposed on a gantry.

Figure 11:
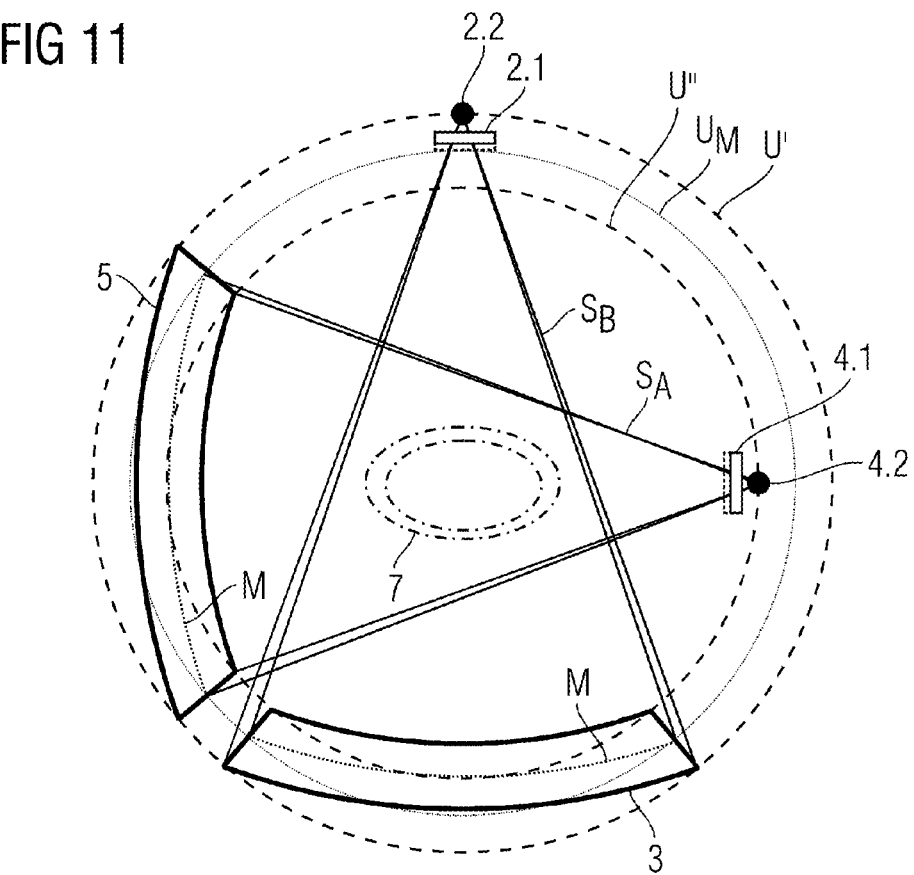
FIG. 11 shows a schematic 3D view of a dual-source CT system with focal points running on different peripheral circles and mutually restricted beam cones.
Figure 12:
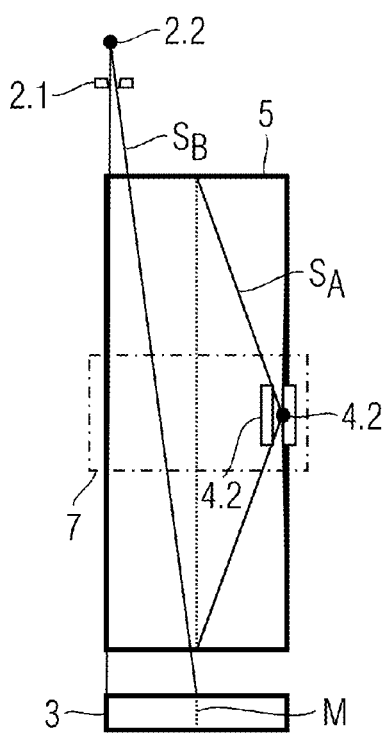
FIG. 12 shows a schematic side view of the CT system from FIG. 11.

FIGS. 11 and 12 show how an improved spatial separation of the beam cone SA and SB can be achieved by an additional z-offset of the focal points 2.2 and 4.2. The two focal points 2.2 and 4.2 move here on the offset peripheral lines U' and U".

Figure 13:
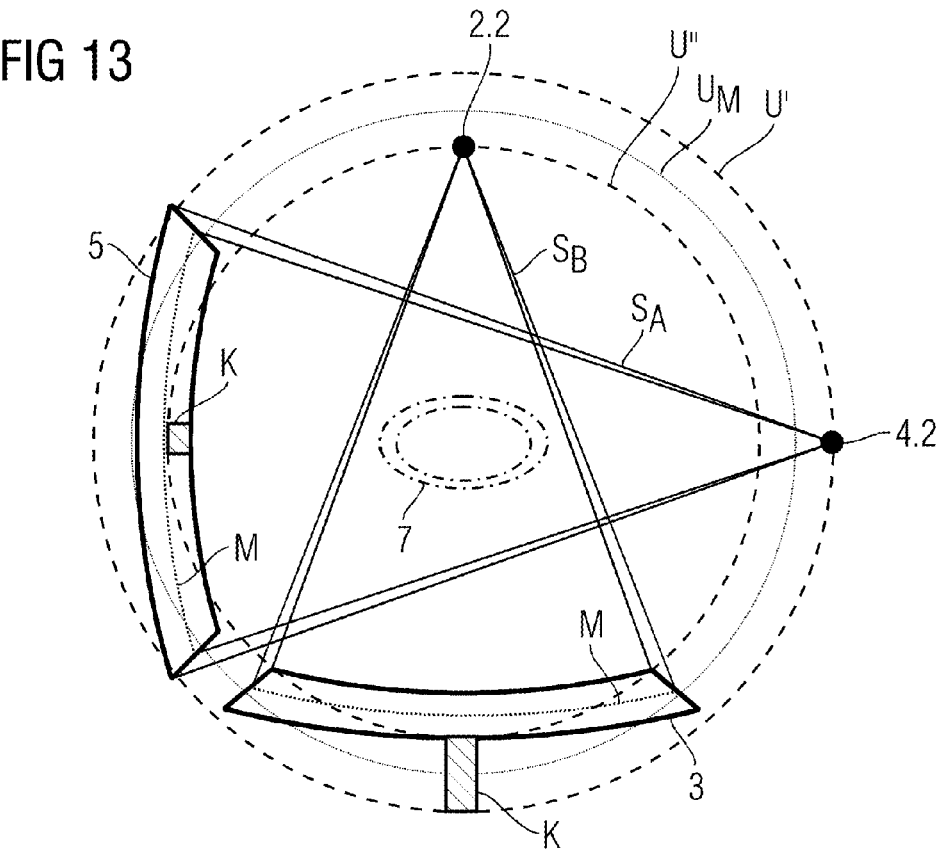
FIG. 13 shows a schematic 3D view of a dual-source CT system according to FIG. 11, nevertheless with tilted detectors.
Figure 14:
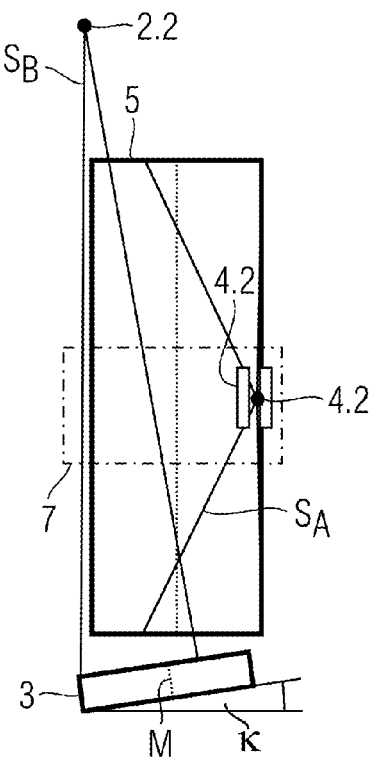
FIG. 14 shows a schematic side view of the CT system from FIG. 13.

In FIGS. 13 and 14, in addition to the z-offset of the focal points, a tilting of the detectors is still shown, wherein an improved alignment of the two-dimensionally acting scattered radiation grid is achieved herewith and the undesired effect of a shading of the beams can be avoided in the scattered radiation grid. The tilting apparatus shown symbolically on the detector 3 is provided with reference character K. The tilting of the detector 3 about the angle κ can be particularly easily seen in FIG. 14.

Reference is also made to the superimposition of the two radiation bundles not having to take place at the same time within the meaning of the invention, but it may also be particularly advantageous to execute an uneven superimposition of the radiation bundle. If the two emitter-detector systems are for instance operated inventively with different x-ray energy spectrum, it may be particularly favorable to superimpose the radiation bundle with the higher average radiation energy more significantly than the radiation bundle with the lower average radiation energy. An improved dose weighting can be achieved in this way. By way of example, the radiation bundle with 100 kVp can be assigned to a detector with effectively 54 lines and the radiation bundle with 140 kVp can be assigned to a detector with effectively used 41 lines. A desired dose weighting of 1:1.3 is herewith produced during the scanning process.

Figure 15:
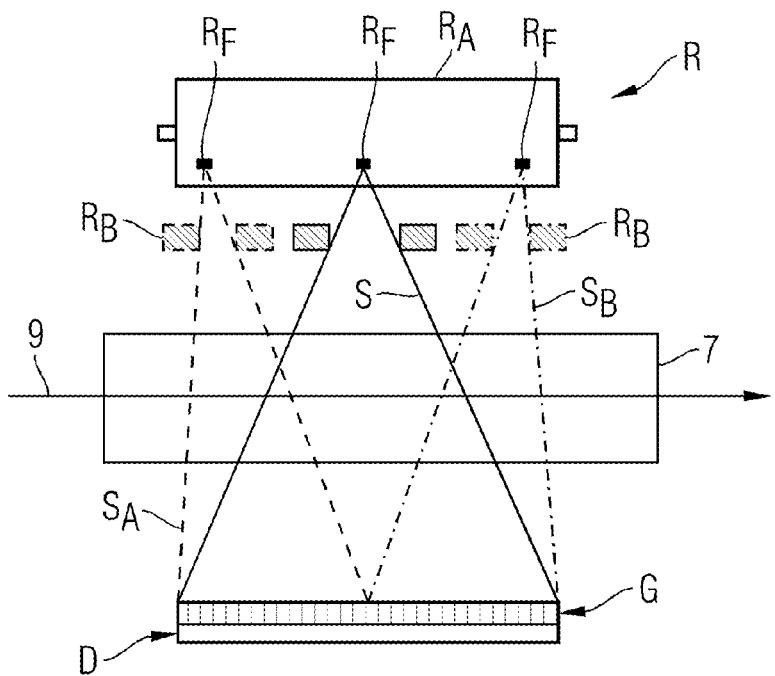
FIG. 15 shows a schematic sectional representation through an emitter-detector system with an x-ray tube having a variable focal point in the z-direction and FIG. 16 shows a 3D view of a radiation grid which operates in a two-dimensional manner across a detector.

As an example of a CT system with a x-ray tube having a variable focal point in the z-direction, FIG. 15 indicates a schematic section through an emitter-detector system along the system axis 9, on which a examination object 7 is shown. In this way the x-ray tube R has a cylindrical anode RA on which, different radiation bundles SA, S, SB are generated depending on the setting of the diaphragms RB and the focal point RF (=focus) on the anode R. As apparent from the Figure, the radiation bundle S can be adjusted for conventional operation such that this irradiates the detector D over the entire z-width, or alternatively a marginal focal point RF can be selected and the diaphragms RB adjusted accordingly such that laterally aligned radiation bundles SA or SB develop, which only partially irradiate the detector D with the scattered radiation grid G arranged thereover and operating in a two-dimensional manner.

Figure 16:
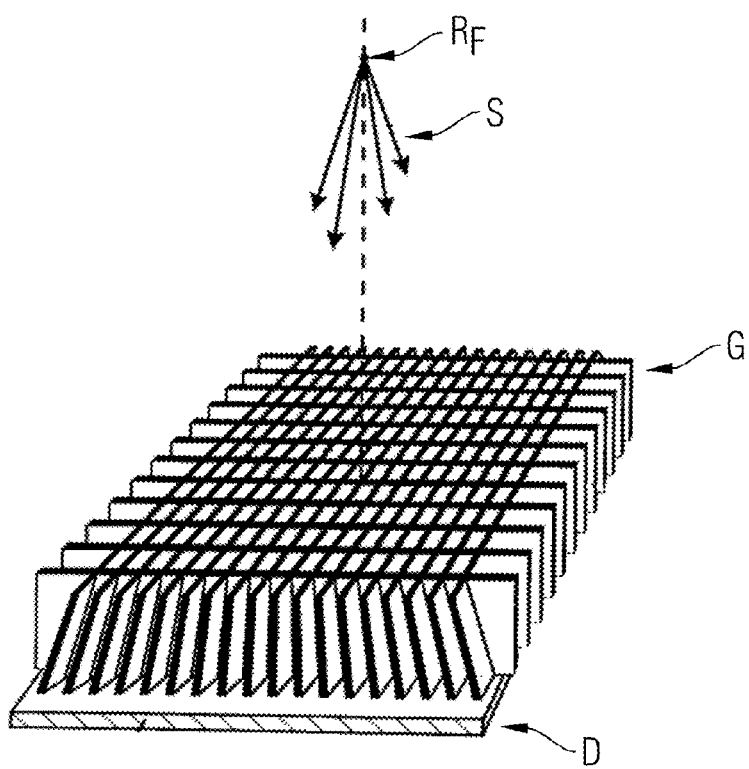

To clarify the scattered radiation grid G operating in a two-dimensional manner, such a scattered radiation grid is shown in FIG. 16 in a three-dimensional view across a detector D. As apparent, the individual shafts of the radiation grid G are aligned here in accordance with the typical alignment of a radiation bundle S originating from a focal point RF.

It is therefore proposed overall with embodiments of the invention, within the scope of an x-ray CT scan with a dual-source system, to delimit the two radiation bundles by diaphragms such that these radiation bundles, at least in the examination object, are free of mutual points of intersection. Accordingly, a dual-source CT system is also proposed, which includes at least one device/module to control the radiation-delimiting diaphragms, which delimit and align the two radiation bundles such that these radiation bundles, at least in the examination object, run freely from mutual points of intersection.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. A method of X-ray CT scanning of an examination object using two emitter-detector systems arranged at different angles on a shared gantry of a CT system, each of the two emitters including a focal point and each of the two detectors being embodied as a multi-row detector with a scattered radiation grid operating in a two-dimensional manner, the method comprising:
   generating, during the scanning process between each of the respective focal points and an opposing one of the two detectors of each of the two emitter-detector systems, a radiation bundle diverging in two dimensions by delimiting emitter-side diaphragms mounted on the gantry in a fixed position relative to a respective emitter, wherein the two radiation bundles are adjustably delimited by the diaphragms to irradiate an entire surface of a respective multi-row detector or less than an entire surface of the respective multi-row detector and, such that the radiation bundles are free of mutual points of intersection at least in the examination object; and
   optimizing alignment of the emitter-detector systems by tilting at least one multi-row detector relative to the system axis and the gantry and displacing at least one multi-row detector in the z-direction to thereby optimize alignment of the at least one emitter-detector system.

2. The method of X-ray CT scanning of claim 1, wherein the two focal points run on a shared peripheral line.

3. The method of X-ray CT scanning of claim 1, wherein the two focal points run onto two separate peripheral lines.

4. The method of X-ray CT scanning of claim 3, wherein the two separate peripheral lines of the focal points form circular surfaces, each running offset toward a center line of the detectors when viewed in the z-direction.

5. The method of X-ray CT scanning of claim 4, wherein the two radiation bundles are delimited in the z-direction such that they only irradiate part of their multi-row detector in each instance.

6. The method of X-ray CT scanning of claim 5, wherein only the irradiated part of the detectors is used in each instance for determining the radiation attenuation.

7. The method of X-ray CT scanning of claim 4, wherein the focal points are set with respect to their z-coordinates within the irradiated part of the detectors of the associated emitter-detector system.

8. The method of X-ray CT scanning of claim 1, wherein the two radiation bundles each respectively irradiate their respective detectors entirely with respect to the peripheral direction.

9. The method of X-ray CT scanning of claim 3, wherein at least one of the detectors is aligned by tilting with respect to the z-axis toward its focal point which is offset in the z-direction.

10. A dual-source CT system for scanning an examination object, comprising:
    two emitter-detector systems, arranged at different angles on a gantry, each including
       at least one x-ray tube which forms a respective focal point during operation and which is configured to rotate on a peripheral line about a system axis running in the z-direction, and
       a multi-row detector, configured to rotate about the system axis, detector rows of the multi-row detector being configured to run in the peripheral direction, the multi-row detector including a scattered radiation grid configured to operate in a two-dimensional manner,
       at least one emitter-side diaphragm arranged on the gantry at a fixed position relative to the at least one x-ray tube, wherein, based on a respective focal point, a radiation bundle delimited by the at least one diaphragm is configured to be aligned toward a respectively assigned multi-row detector; and
    a controller, configured to control the diaphragms to adjustably delimit and align the two radiation bundles such that the radiation bundles irradiate an entire surface of a respective multi-row detector or less than an entire surface of the respective multi-row detector and thereby avoid mutual points of intersection of the respective radiation bundles, wherein a tilting apparatus is provided for at least one multi-row detector, configured to tilt the multi-row detector relative to the system axis and the gantry and a displacement apparatus is provided for at least one emitter-detector system, which is configured to displace at least one multi-row detector in the z-direction to thereby optimize alignment of the at least one emitter-detector system.

11. The dual-source CT system of claim 10, wherein a focal point, positionable differently in the z-direction, is provided for at least one multi-row detector.

12. The dual-source CT system of claim 10, wherein at least two emitters, each with a differently positioned focal point in the z-direction, are provided for at least one multi-row detector.

13. The dual-source CT system of claim 10, wherein an emitter is provided with a focal point which is displaceable in the z-direction for at least one multi-row detector.

14. The dual-source CT system of claim 13, wherein the at least one emitter includes a rotatable, cylindrical anode with an axis of rotation.

15. The dual-source CT system of claim 14, wherein the axis of rotation of the cylindrical anode is arranged in parallel with the system axis.

16. The dual-source CT system of claim 14, wherein the axis of rotation of the cylindrical anode is tilted at the same angle with respect to the system axis, as the assigned multi-row detector.

17. The dual-source CT system of claim 10, wherein a displacement apparatus is provided for at least one emitter-detector system, which is configured to displace at least one multi-row detector with its focal point in the z-direction.

18. The dual-source CT system of claim 10, wherein, a displacement apparatus is provided for at least one emitter-detector system, which is configured to displace at least one emitter-detector system in the z-direction.

19. The method of X-ray CT scanning of claim 5, wherein the focal points are set with respect to their z-coordinates within the irradiated part of the detectors of the associated emitter-detector system.

20. The method of X-ray CT scanning of claim 6, wherein the focal points are set with respect to their z-coordinates within the irradiated part of the detectors of the associated emitter-detector system.

21. The method of X-ray CT scanning of claim 1, wherein the two radiation bundles are delimited in the z-direction such that they only irradiate part of their multi-row detector in each instance.

22. The method of X-ray CT scanning of claim 2, wherein the two radiation bundles are delimited in the z-direction such that they only irradiate part of their multi-row detector in each instance.

23. The method of X-ray CT scanning of claim 3, wherein the two radiation bundles are delimited in the z-direction such that they only irradiate part of their multi-row detector in each instance.

24. The dual-source CT system of claim 11, wherein at least two emitters, each with a differently positioned focal point in the z-direction, are provided for at least one multi-row detector.

25. The dual-source CT system of claim 11, wherein an emitter is provided with a focal point which is displaceable in the z-direction for at least one multi-row detector.

* * * * *